United States Patent
Guerin et al.

(10) Patent No.: US 10,661,091 B2
(45) Date of Patent: May 26, 2020

(54) SYSTEM AND METHOD FOR HYPERTHERMIA TREATMENT USING RADIOFREQUENCY PHASED ARRAYS

(71) Applicants: Bastien Guerin, Cambridge, MA (US); Lawrence L. Wald, Cambridge, MA (US); Bruce Rosen, Lexington, MA (US)

(72) Inventors: Bastien Guerin, Cambridge, MA (US); Lawrence L. Wald, Cambridge, MA (US); Bruce Rosen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 1240 days.

(21) Appl. No.: 14/668,393

(22) Filed: Mar. 25, 2015

(65) Prior Publication Data
US 2015/0273230 A1   Oct. 1, 2015

Related U.S. Application Data

(60) Provisional application No. 61/970,722, filed on Mar. 26, 2014.

(51) Int. Cl.
*A61N 1/40* (2006.01)
*G01R 33/48* (2006.01)
(Continued)

(52) U.S. Cl.
CPC .............. *A61N 1/403* (2013.01); *A61B 34/10* (2016.02); *G01R 33/48* (2013.01); *A61B 2034/101* (2016.02); *G01R 33/5612* (2013.01)

(58) Field of Classification Search
CPC .................................................. A61N 1/403
See application file for complete search history.

(56) References Cited

U.S. PATENT DOCUMENTS

2010/0145420 A1* 6/2010 Zhu ..................... A61B 5/055
                                                                607/103
2011/0043205 A1* 2/2011 Graesslin ........... G01R 33/5612
                                                                324/307

FOREIGN PATENT DOCUMENTS

WO     WO 97/07736 A1    3/1997

OTHER PUBLICATIONS

Lee et al., "Local SAR in Parallel Transmissin Pulse Design". Magn Reson Med., Jun. 2012; 67(6) pp. 1566-1578. Document provided is notated as pp. 1-25.*

(Continued)

*Primary Examiner* — James M Kish
(74) *Attorney, Agent, or Firm* — Quarles & Brady LLP

(57) ABSTRACT

Systems and methods for designing parallel transmission radiofrequency (RF) pulses for use in a RF treatment. The methods include selecting a target region in a subject, and providing a plurality of specific absorption rate (SAR) matrices for estimation of SAR at locations within the subject. The methods also include determining a first set of SAR matrices for locations in the target region using the provided SAR matrices, and determining a second set of SAR matrices for locations not in the target region using the provided SAR matrices. The methods further include designing a plurality of RF pulses for achieving a target power deposition in the target region by using the first set of SAR matrices and the second set of SAR matrices in an optimization that determines a set of RF waveforms that produce a target average local SAR using the first set of SAR matrices while minimizing a local SAR and a global SAR using the second set of SAR matrices.

20 Claims, 10 Drawing Sheets

(51) Int. Cl.
*A61B 34/10* (2016.01)
*G01R 33/561* (2006.01)

(56) References Cited

OTHER PUBLICATIONS

S.P. Boyd and L. Vandenberghe, "Convex Optimization," Cambridge Univ. Press, 2004, 9 pages.
G. Eichfelder and M. Gebhardt, "Local specific absorption rate control for parallel transmission by virtual observation points," Magnetic Resonance in Medicine, 2011; 66(5): 1468-1476.
A. Sbrizzi et al., in "Fast design of local N-gram specific absorption rate—optimized radiofrequency pulses for parallel transmit systems," Magnetic Resonance in Medicine, 2012; 67(3):824-834.

\* cited by examiner

Body Heating with 8 Channels
*Global SAR constraint of healthy tissues (no local SAR constraint)*

21 MHz
Location #3, arms not included in treat. plan.

63 MHz
Location #3, arms not included in treat. plan.

128 MHz
Location #3, arms not included in treat. plan.

Brain Heating with 16 Channels
*Global SAR constraint of healthy tissues (no local SAR constraint)*

297MHz
Location #1

297MHz
Location #2

SYSTEM AND METHOD FOR HYPERTHERMIA TREATMENT USING RADIOFREQUENCY PHASED ARRAYS

CROSS-REFERENCE TO RELATED APPLICATIONS

This application claims the benefit of U.S. Provisional Patent Application Ser. No. 61/970,722, filed on Mar. 26, 2014, and entitled "SYSTEM AND METHOD FOR HYPERTHERMIA TREATMENT USING RADIOFREQUENCY PHASED ARRAYS."

STATEMENT REGARDING FEDERALLY SPONSORED RESEARCH

This invention was made with government support under EB006847 awarded by the National Institutes of Health. The government has certain rights in the invention.

BACKGROUND

The present disclosure relates generally to systems and methods for magnetic resonance imaging (MRI), in particular, to systems and methods for designing parallel transmission (pTx) radiofrequency (RF) pulses for focused tissue treatment.

Outside surgical interventions, treatments for tissue abnormalities, such as malignant tumors, typically include techniques aimed at directly killing cells using high energy beams of ionizing particles, such as photons, electrons, protons and other ions. Although a variety of conformal approaches have been developed, aiming to minimize damage to healthy tissues due to radiation exposure, such systems and methods maintain considerable risks and side-effects, especially for deep-seated targets. For example, in the case of photons, deposition of ionizing energy is peaked closer to the surface, in dependence of beam energy, resulting in significant energy deposition along the path of the beam. By contrast, protons, and other charged particles, exhibit strongly non-linear absorption profiles, or Bragg peaks, in tissue, whereby strong energy deposition occurs at depth with little absorption occurring closer to the tissue surface. Nevertheless, such absorption profiles include tails that are still very significant, and result in death or injury to healthy tissues outside the target.

In addition, ionizing radiation presents further issues on account of difficulties associated with dose monitoring. For example, computer simulations are commonly used to predict the dose distribution, but these are subject to programming errors, errors in the segmented models of the subject, and incorrect registration between the subject and model. Also, monitoring of response to treatment may be done using CT, PET and MR imaging after the treatment, but there are no easy ways to verify the dose during a treatment session. Furthermore, ionizing radiation only provides for lethal killing of cells, and so other treatments, such as hyperthermia, are not possible with this technique.

By contrast, focused ultrasound waves can achieve local "point" heating in portions of a subject anatomy, such as the brain or torso, and can therefore be used as alternative approaches for hyperthermia treatment. However, a significant drawback of such methods stem from the nature of propagation of ultrasound energy in the body. For example, in the case of non-invasive brain treatment, ultrasound waves must pass through the skull. Since the skull acts as a sound wave insulator, achieving significant heating inside the brain necessitates increasing the power of the ultrasound device. As a result, most of the additional energy is dissipated in the skull, as well as outer skin and fat layers of the head, and not in the brain. This may cause significant and undesirable heating of the skull, which may necessitate extraneous cooling systems methods. In fact, temperature increases in the skull may be many times larger than that of the target.

By contrast, RF-based hyperthermia treatment generally involves heating target cells by exposing them to an intense RF field. Unlike sound waves, however, radiofrequency (RF) waves are not stopped by a skull, and thus treatment with RF waves may not significantly affect a skull or any other non-target tissue. In some cases, it may be desirable to achieve a modest temperature rise that would not kill specific cells, such as tumor cells, but instead render them more responsive to specific biological agents. For example, when used in conjunction, chemotherapy treatment, RF-based hyperthermia may allow for reduction in chemotherapy dose, thus reducing side effects, while increasing efficiency. Therefore, unlike for the case of ionizing particles, the intensity of RF-based hyperthermia treatment can be adjusted continuously to induce smaller temperature increases that warm the tumor cells, or larger temperature rises that would destroy them. As a result, the ability to continuously adjust the intensity of heating can be used to adapt the treatment to the patient-specific requirements of personalized medicine.

Previously, parallel transmission (pTx) RF pulse design algorithms have been proposed, in the context of magnetic resonance imaging applications, for achieving uniform excitation of spins across a field of view. Due to versatility on account of a large number of degrees of freedom, pTx RF pulse techniques have provided important approaches toward addressing RF and static field inhomogeneity issues, which are particularly problematic at high magnetic fields. Specifically, electromagnetic (EM) simulations have shown that the interference of electric fields created by multiple RF channels can deposit large amounts of energy, as measured by specific absorption rates (SARs), with multiple focal locations in the body. When not controlling local SAR explicitly in the pTx pulse design process (i.e. when controlling global SAR or pulse power), local SAR in pTx is often found to be 5 to 10 times greater than in single channel excitations. As such, it is generally the goal of previous RF pulse design algorithms to find excitation patterns that minimize specific absorption rate (SAR) requirements, in accordance with regulated limits, while optimizing RF pulse performance and adhering to hardware constraints.

It would therefore be desirable to provide systems and methods for designing pTx RF pulses for use in RF treatment applications that overcome the shortcomings of currently available methods.

SUMMARY

The present invention overcomes the aforementioned drawbacks by providing a system and method directed to use of RF phased arrays, such as those of a MRI system, to achieve parallel transmission (pTx) of RF pulses designed for maximal energy deposition in a target region within an anatomy of a subject, while minimizing deposition in non-target regions. Specifically, a RF pulse optimization process is disclosed that takes into consideration a heating objective in conjunction with local SAR, global SAR requirements as well as hardware power constraints.

In accordance with one aspect of the disclosure, a method is provided for designing parallel transmission radiofrequency (RF) pulses for use in a RF treatment. The method includes selecting a target region in a subject and providing a plurality of specific absorption rate (SAR) matrices for estimation of SAR at locations within the subject. The method also includes determining a first set of SAR matrices for locations in the target region using the provided SAR matrices, and determining a second set of SAR matrices for locations not in the target region using the provided SAR matrices. The method further includes designing a plurality of RF pulses for achieving a target power deposition in the target region by using the first set of SAR matrices and the second set of SAR matrices in an optimization that determines a set of RF waveforms that produce a target average local SAR in the treatment region using the first set of SAR matrices while minimizing a local SAR and a global SAR outside the treatment region using the second set of SAR matrices.

In accordance with another aspect of the disclosure, a magnetic resonance imaging (MRI) system for is provided. The system includes a magnet system configured to generate a polarizing magnetic field about at least a portion of a subject arranged in the MRI system, and a plurality of gradient coils configured to apply at least one magnetic field gradient to the polarizing magnetic field. The system also includes a radio frequency (RF) system including at least one RF coil configured to apply an RF field to the subject and to receive magnetic resonance signals therefrom, and a computer programmed to select a target region in a subject, and provide a plurality of specific absorption rate (SAR) matrices that define estimates of SAR at locations within the subject. The computer is also programmed to determine a first set of SAR matrices for locations in the target region using the provided SAR matrices and determine a second set of SAR matrices for locations not in the target region using the provided SAR matrices. The computer is further programmed to design a plurality of RF pulses for achieving a target power deposition in the target region based on an optimization that uses the first set of SAR matrices and the second set of SAR matrices to determine a set of RF waveforms that direct the parallel transmitter to generate an RF field that achieves a target average local SAR in the target region while minimizing a local SAR and a global SAR outside the target region.

The foregoing and other advantages of the invention will appear from the following description.

DETAILED DESCRIPTION

Figure 1:
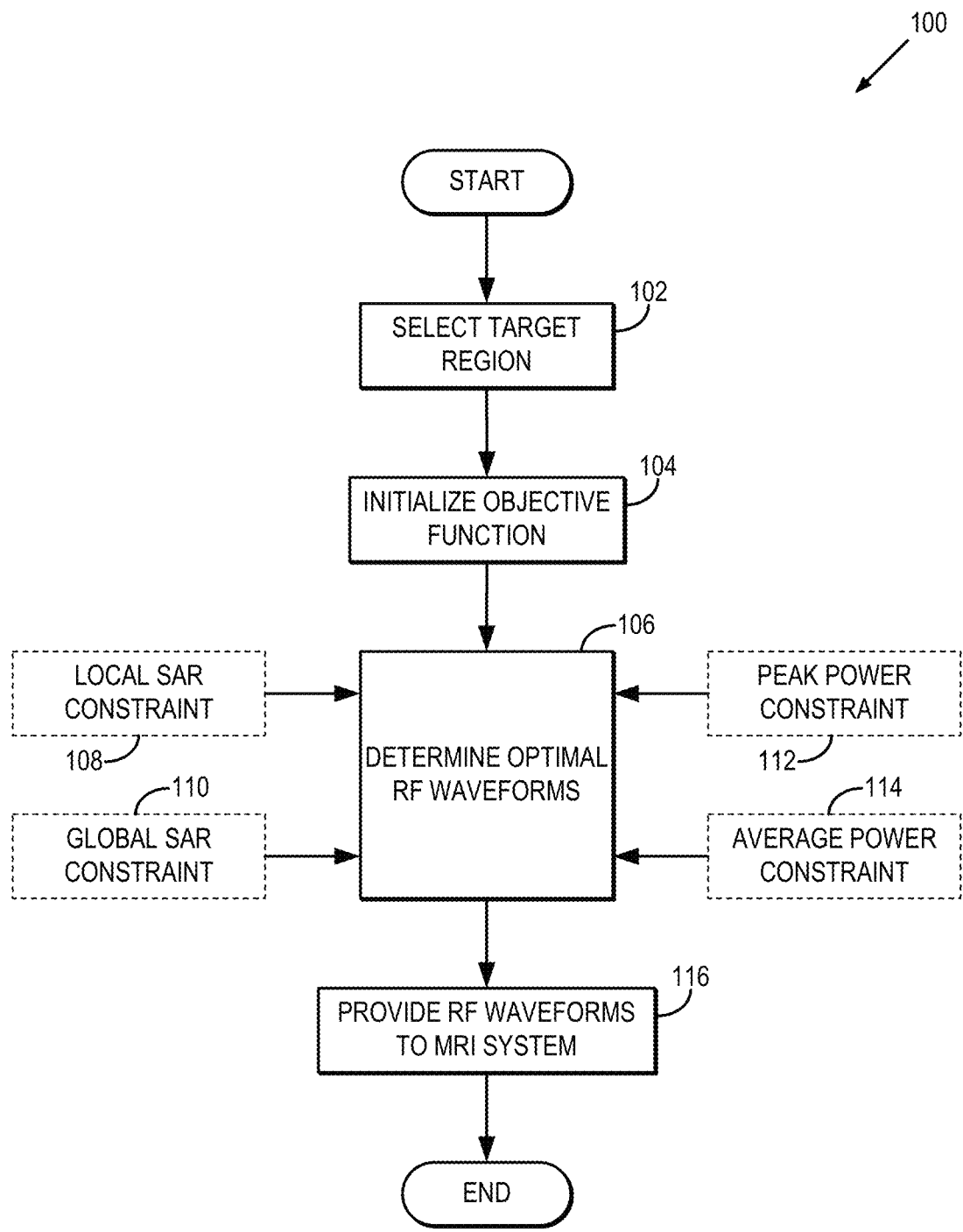
FIG. 1 is a flowchart setting forth the steps of an example of a method for designing parallel transmission RF pulses.

Described here are systems and methods directed to parallel transmission (pTx) of radiofrequency (RF) radiation to a subject anatomy via RF phased arrays for purposes of RF treatment and monitoring. As will be described below, the systems and methods of the present invention may be configured for controlling or optimizing RF energy deposition, and spatiotemporal excitation profiles, in regions of interest within a subject by determining a set of RF waveforms that achieve desired power deposition patterns using an optimization process. For instance, an RF pulse design algorithm may be implemented to design RF pulses that will have desired constructive and destructive interference patterns of electric field intensities when generated using an RF phased coil array. This pulse design can be achieved by including constraints in an RF pulse optimization process, which guarantee that energy delivered to the subject using transmitted RF pulses adheres to RF treatment objectives and is consistent with specific absorption rate (SAR) limits and power capabilities of the hardware system(s) employed. For example, FDA and SEC limits for SAR in healthy tissues allow for 8 W/kg maximum (local SAR) and 4 W/kg average (global SAR) in a subject torso, while for a head, these are 8 W/kg maximum and 3 W/kg average. Such optimization process may facilitate achieving a best possible distribution of RF waveforms for desired or target power absorption profiles, resulting, for example, in local temperature elevations in target regions, or tissues, with minimum effects to non-target regions, or tissues.

In some embodiments, RF pulses designed by the present systems and method scan be subject-specific RF pulses that are determined using models generated by subject-specific data. These subject-specific pulses provide more precise results, albeit at the cost of additional computation time. As an example, for a subject-specific pulse design, electric fields created by a RF phased array should be computed specifically for the subject anatomy. This process includes creating a model of the subject and simulating the propagation of EM fields created by RF phased arrays using that model. Different approaches can be used to generate a subject model, as well as for simulation of the EM fields, and the present invention is not limited to any one of them. In some other embodiments, RF pulses can be designed using a generic subject model, which would reduce the required time at the cost of patient-specific accuracy.

Using the subject model, whether subject-specific or generic, spatial matrices indicative of energy absorption sensitivities at discrete locations in the subject can be computed. These matrices allow calculation of the local energy deposition as a function of the RF waveforms played out using the RF phased arrays. In this manner, an RF treatment planning may be formulated by way of an optimization process for designing RF pulses using these matrices, subject to local, and global SAR limits as well as hardware constraints, as mentioned.

When using several transmit channels to excite the MR signal, SAR at a location, r, is computed from the knowledge of the electric fields $E_1(r), \ldots, E_C(r)$ created by the C transmit channels; the RF waveforms played on each of these channels; the conductivity, $\sigma(r)$; and density $\rho(r)$, according to the following:

$$SAR(r) = \frac{\sigma(r)}{2\rho(r)} \frac{1}{T} \int_0^T \left\| \sum_{c=1}^C E_c(r, t) \right\|^2 dt; \quad (1)$$

which can be approximated as $$SAR(r) = \frac{\sigma(r)}{2\rho(r)} \frac{1}{N_T} \sum_{i=1}^{N_T} b(i\Delta t)^H Q(r) b(i\Delta t). \quad (2)$$

In Eqn. (2), $b(i\Delta t)$ is the vertical concatenation of RF values played on all channels at time $i\Delta t$; $\{\ldots\}^H$ indicates the Hermitian transpose operator; T is the pulse length; $N_T$ is the number of RF samples; and $Q(r)$ is the correlation matrix of electric fields created by all channels at the location, r. SAR averaging over a given volume (e.g., a ten gram or one gram volume) as prescribed by the FDA can be done at the level of the correlation matrices, $Q(r)$ by summing the original matrices contained in the averaging volume. Eqn. (2) is thus valid even when performing SAR averaging. The material properties and other constants are incorporated in the definition of the correlation matrix, $Q(r)$ to simplify notations.

In theory, explicit control for local SAR in the design of MRI pulses should be performed by controlling SAR at every position, r, of the body model used to compute the electric fields. Assuming an average tissue density of 1000 kg/m³ body, 1 g (10 g) of tissue corresponds to a volume $10^{-6}$ m³ ($10^{-5}$ m³). For the averaging process to be reasonably accurate, at least 50 Q-matrices would need to be summed, which means that the linear resolution of the body model would need to be at least 2.7 mm (5.8 mm). At these resolutions, typical body models contain hundreds of thousands of voxels. Controlling SAR at so many locations would make the pulse design process extremely slow and, therefore, not applicable in the clinic. To solve this problem, the method of the present invention controls SAR in the entire body using a compression of the original SAR matrices, $SAR(r)$ to reduce the number of evaluation points.

By way of example, one method for compressing the SAR matrices, $SAR(r)$ can include forming a significantly smaller set of virtual observation points ("VOPs"). The compression of the SAR matrices, $SAR(r)$, can be carried out as described by G. Eichfelder and M. Gebhardt in "Local specific absorption rate control for parallel transmission by virtual observation points," *Magnetic Resonance in Medicine*, 2011; 66(5): 1468-1476, which is incorporated herein by reference. The VOP compression scheme allows for the reduction of the number of SAR matrices by a factor of 300 or more, while ensuring that the local SAR estimation error associated with the compression process is an overestimation. The safety margin afforded by this overestimation is a beneficial feature of the algorithm. Another example of how the SAR matrices, $SAR(r)$, can be compressed is to use the compression method described by A. Sbrizzi, et al., in "Fast design of local N-gram specific absorption rate—optimized radiofrequency pulses for parallel transmit systems," *Magnetic Resonance in Medicine*, 2012; 67(3):824-834, which is incorporated herein by reference. Unlike the VOP method, this compression technique does not guarantee that the SAR error is an overestimation. Although the succeeding description is provided with respect to using VOPs, it will be appreciated by those skilled in the art that the VOPs can be readily exchanged with other compressed samplings of the SAR matrices, $SAR(r)$.

Other popular model reduction methods, like truncated singular value decomposition (SVD), could be used to reduce the number of SAR matrices, but these methods typically result in local SAR estimation errors that are sometimes positive and sometimes negative. That is, in some cases these methods underestimate local SAR, which is potentially harmful to the patient. The local SAR overestimation error associated with the VOP compression scheme is bounded by a user-defined maximum allowed error that indirectly controls the number of VOPs. A tight control of local SAR thus requires more VOPs than a loose one.

Figure 5:
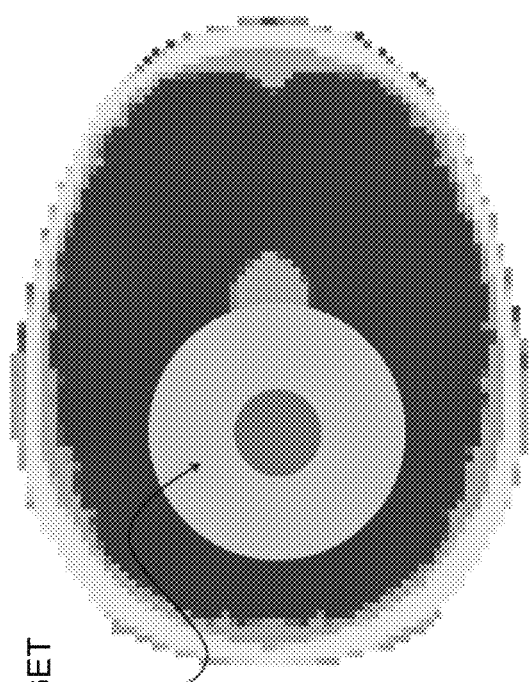
FIG. 5 is a schematic illustration of example target and non-target regions in a subject.
Figure 5:
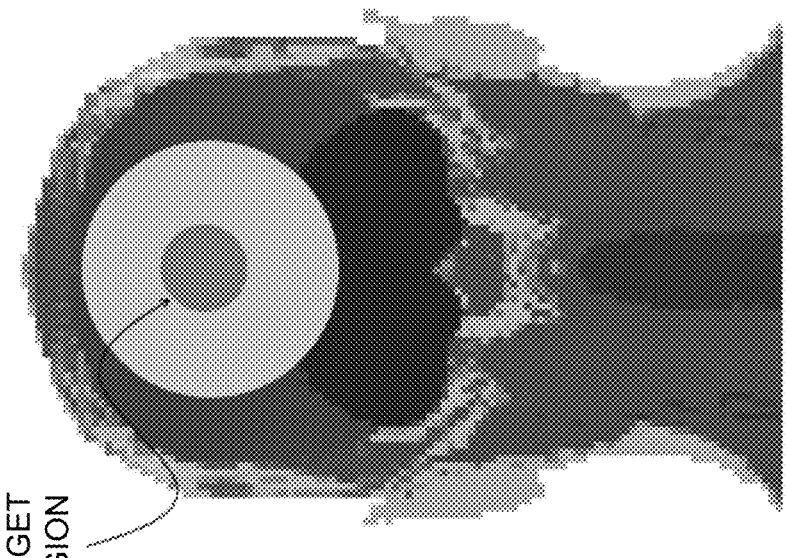

Optimization of the RF treatment, via optimally designed RF pulses, involves balancing many opposing goals in order to find the best tradeoff between those opposing goals. For example, one tradeoff that is balanced is the heating of the target regions or tissues while minimizing power deposition and heating provided to healthy tissues or any other non-target regions (FIG. 5). As a specific example, the following objective function, which aims to maximize an RF energy deposition in target locations, can be utilized when designing RF pulses in accordance with some embodiments of the invention:

$$\max_b \{ b^H \langle SAR(r) \rangle_{hz} b \}; \quad (3)$$

where $\langle SAR(r) \rangle$ is an average SAR matrix for location r in the target region, or heating zone, and b is the concatenation of the RF waveforms to be computed.

The optimization problem of Eqn. (3) is constrained by the following constraints:

$$\frac{1}{N_T} \sum_{t=1}^{N_T} b(t)^H S_j b(t) \leq SAR_{local}; \quad (4)$$

$$\frac{1}{N_T} \sum_{t=1}^{N_T} b(t)^H \langle S \rangle b(t) \leq SAR_{global}; \quad (5)$$

$$\|b\|_\infty \leq P_{peak}; \text{ and} \quad (6)$$

$$\|b\|_2^2 \leq P_{avg}. \quad (7)$$

These constraints can be described as follows: Eqn. (4) constrains local SAR at every compressed SAR matrix point; Eqn. (5) constrains global SAR; Eqn. (6) constrains peak power for each channel; and Eqn. (7) constrains average power on every channel.

The optimization problem in Eqn. (3) subject to the constraints of Eqns. (4)-(7) is convex. Notably, the quadratic objective to be maximized is convex and the constraints define a convex set because all SAR matrices are semi-definite positive. To solve this optimization problem, a primal/dual interior point algorithm, such as the one described by S. P. Boyd and L. Vandenberghe in *Convex Optimization* (Cambridge Univ. Press, 2004), which is incorporated herein by reference, can be used. Each Newton iteration of such primal/dual procedure can be solved exactly using a Schur complement, which is a square matrix of size equal to the number of unknowns (i.e., the number of RF samples multiplied by the number of channels). Using the Schur complements allows for exact and fast inversion. The convergence of the primal/dual iterations can be tuned by using a Karush-Kuhn-Tucker relaxation parameter that is iteration dependent. For instance, a large relaxation can be used when constraints are active and almost no relaxation can be used when no constraint is active.

Figure 6:
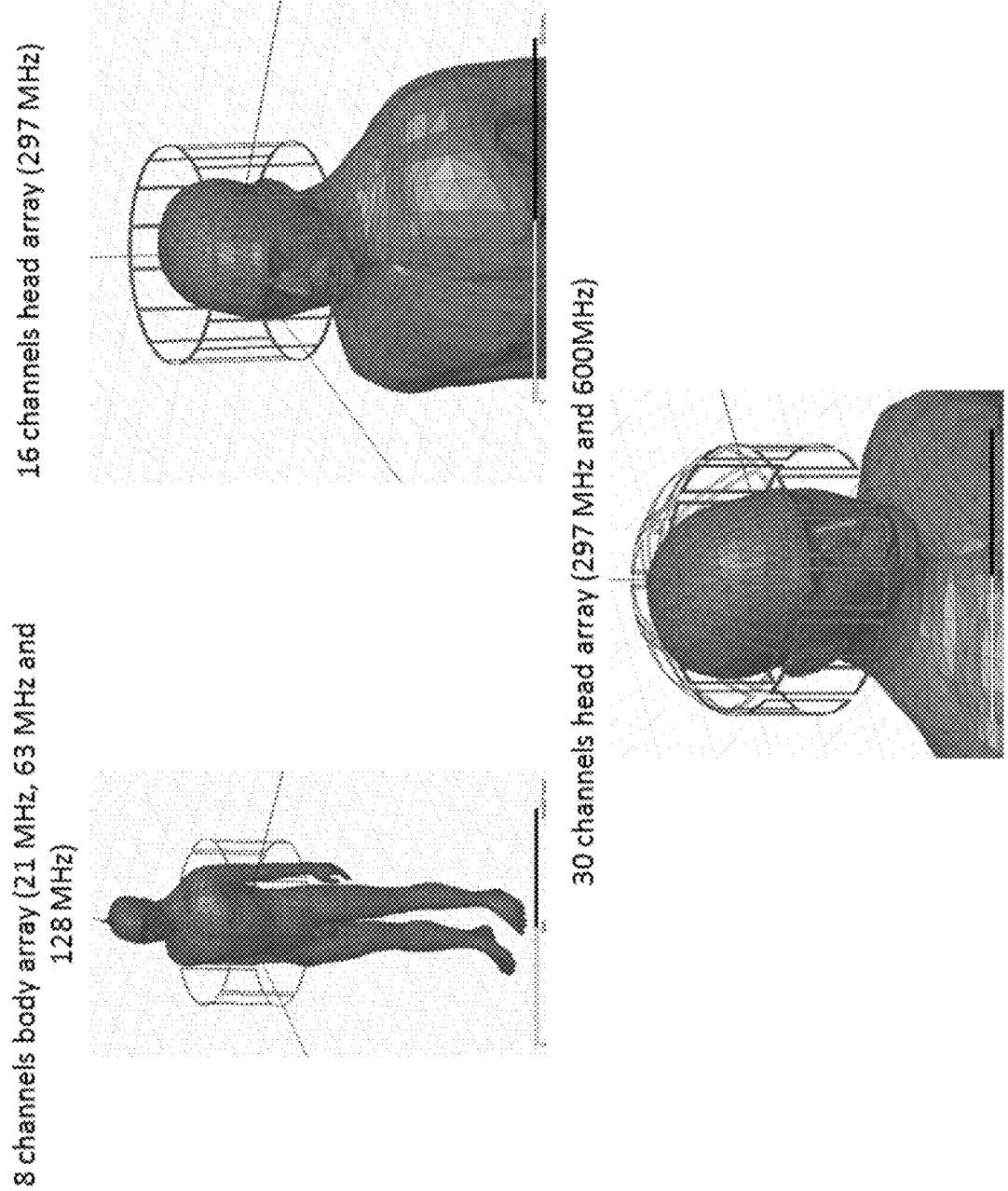
FIG. 6 shows non-limiting examples of RF array configurations.
Figure 7:
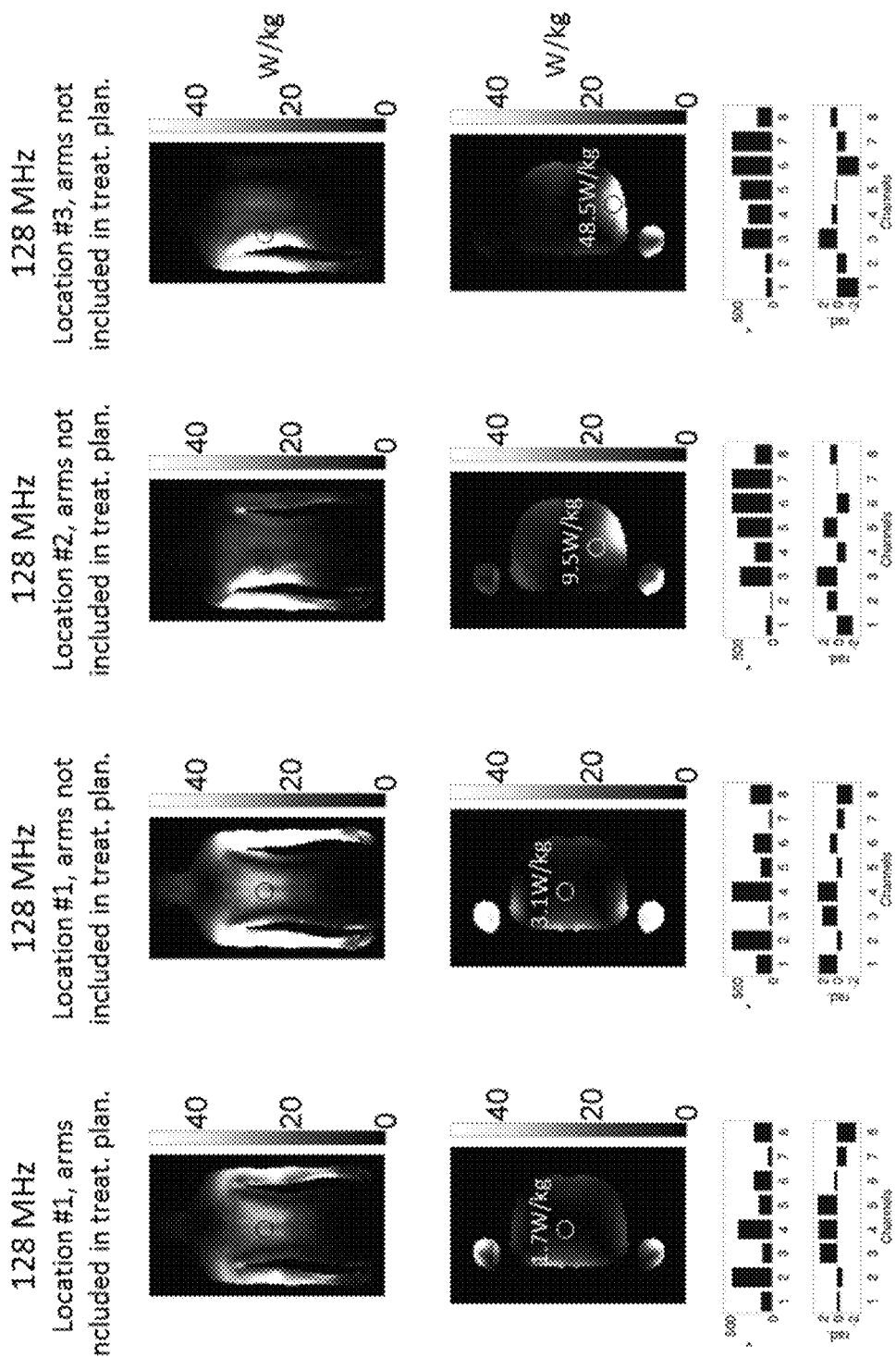
FIG. 7 shows non-limiting example of SAR maps and RF waveforms for maximization of SAR in a heating zone.
Figure 8:
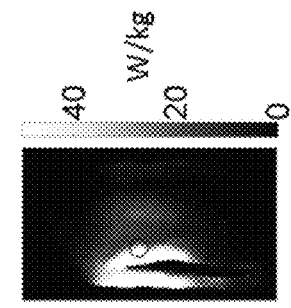
FIG. 8 shows another non-limiting example of SAR maps and RF waveforms for maximization of SAR in a heating zone.
Figure 8:
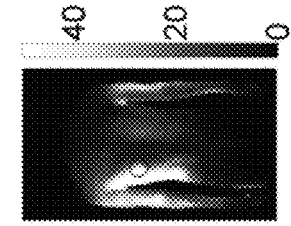
Figure 8:
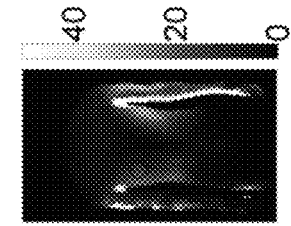
Figure 8:
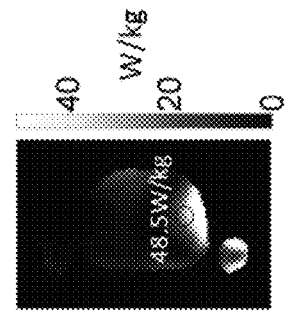
Figure 8:
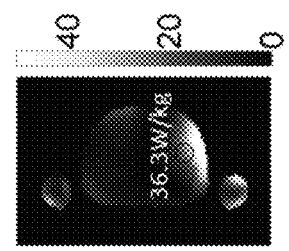
Figure 8:
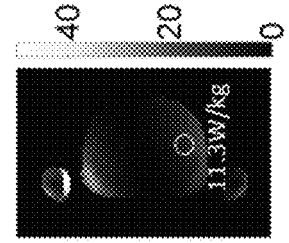
Figure 8:
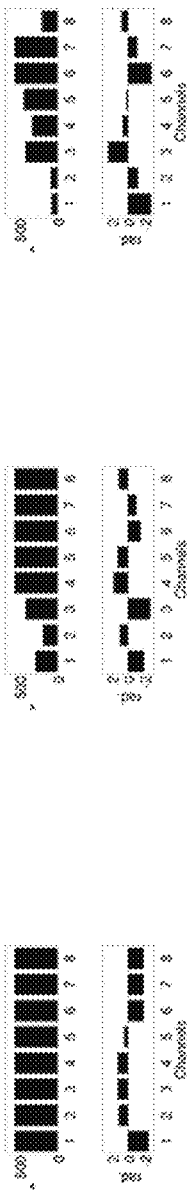
Figure 9:
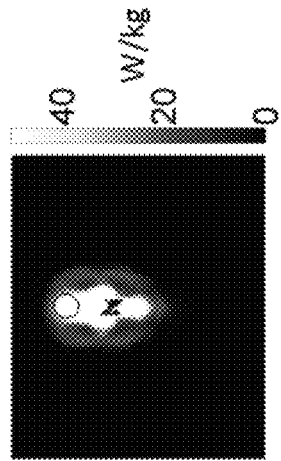
FIG. 9 shows yet another non-limiting example of SAR maps and RF waveforms for maximization of SAR in a heating zone.
Figure 9:
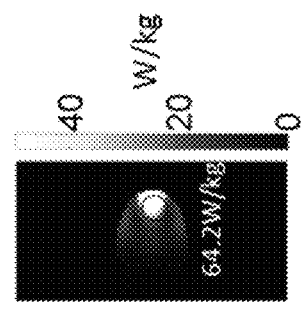
Figure 9:
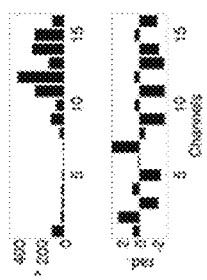
Figure 9:
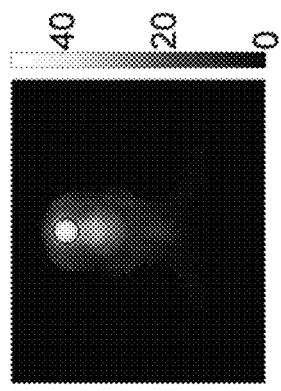
Figure 9:
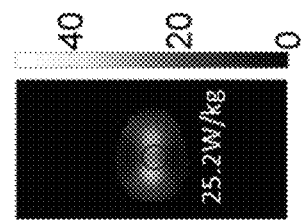
Figure 9:
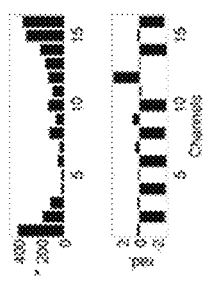
Figure 10:
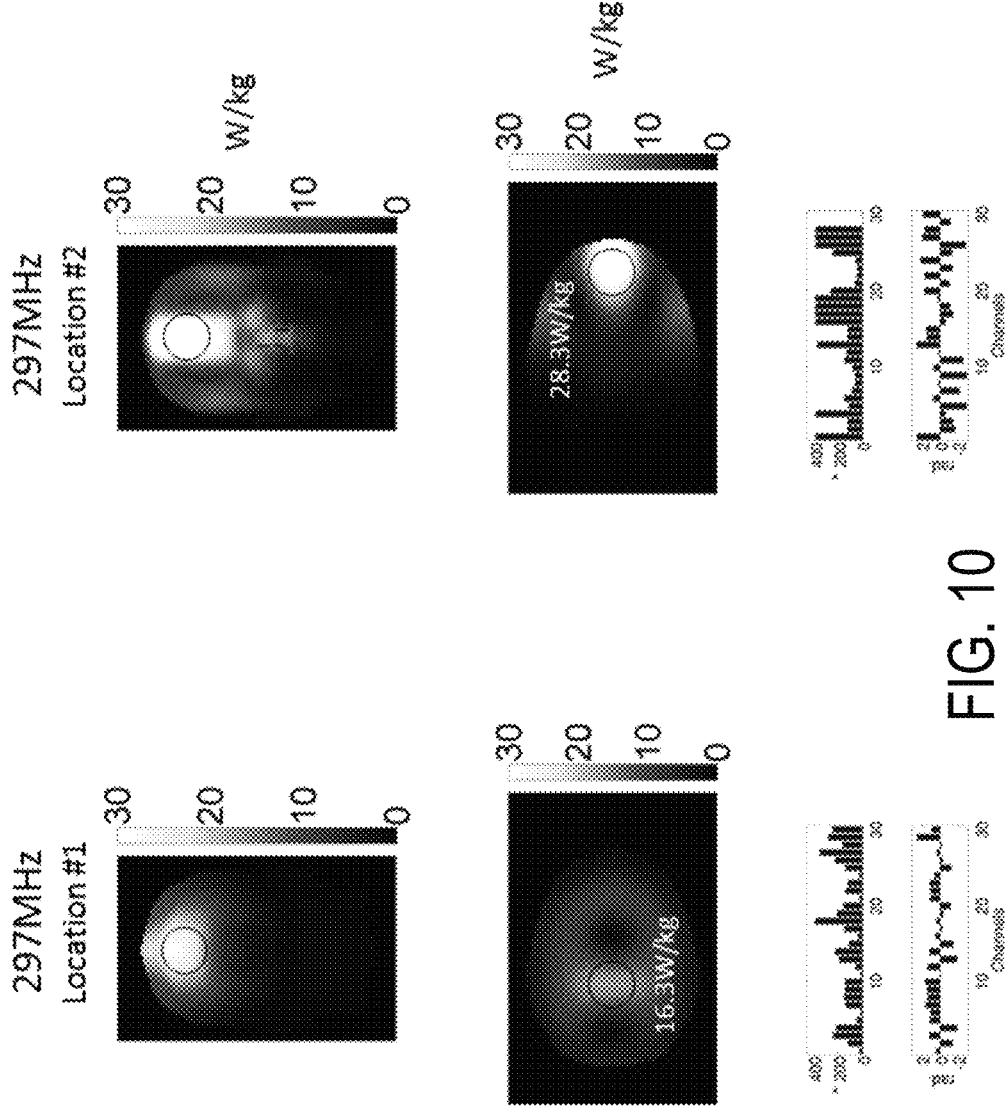
FIG. 10 shows yet another non-limiting example of SAR maps and RF waveforms for maximization of SAR in a heating zone.

In addition, for an RF treatment to be as efficient as possible, an optimization process, in accordance with the present invention, may benefit from adjustment of as many variables as allowable. FIG. 6 shows non-limiting examples of RF array configurations and arrangements. In some aspects, it may be desirable to use RF phased arrays with as many channels as available, since high numbers of transmit channels increase the number of degrees of freedom available to the RF pulse optimization process. Thus, in some configurations, systems for RF treatment may include RF phased arrays with more transmit channels than the number of RF amplifiers accessible, and thus limited possibilities for driving all transmit channels independently.

As such, in addition to capabilities for simultaneous excitation using optimized RF waveforms, the present invention may also include capabilities that would allow for RF excitation using subsets of transmit channels, in accordance with target treatment objectives and corresponding constraints. Specifically, different excitation pulses for each subset of channels may be played out sequentially. For example, if a phased RF array contains 30 transmit channels and only 8 RF amplifiers are available, then subsets of 8 transmit channels out of the 30 available may be excited sequentially during RF treatment by dividing RF excitations into time segments, where there could be as many time segments in the treatment as there are subsets of transmit channels.

Therefore, in some aspects, it may be desirable to have RF pulses associated with some or all time segments or channel subsets optimized jointly, so as to ensure that individual SAR maps intersect maximally in a target region, but overlap as little as possible outside of it. Again, formulation of a multi-subset RF treatment planning includes an optimization process that is solved globally using a constrained optimization algorithms to find the optimal tradeoff between required, or necessary, energy deposition and constraints. Using such an approach typically produces better treatment planning than when computing RF pulses using "ad hoc" empirical methods, which may be suboptimal and do not employ optimization.

Referring now to FIG. 1, a flowchart 100 setting forth the steps of an example of a method for designing parallel transmission RF pulses for RF treatment applications is shown, in accordance with some embodiments of the present invention. The method begins with the selection of at least one target region within a subject at process block 102. In some configurations, imaging or mapping data provided by an MRI system, or any other system, may be used for determining or identifying target regions for selection.

At process block 104 an objective function is initialized using the target region(s) selected. This step may include providing a plurality of specific absorption rate (SAR) matrices that define estimates of SAR at locations within the subject, and may also include determining a first and second set of SAR matrices using the SAR matrices. For instance, the first set of SAR matrices may be associated with locations in the target region and the second set of SAR matrices may be associated with locations in a non-target region, or regions outsides the target region.

Using the objective function, a set of optimal RF waveforms is determined, as indicated at step 106. Preferably, these RF waveforms are determined using the optimization problem set forth in Eqn. (3). This optimization is constrained using one or more of the following constraints: a local SAR constraint, as indicated at 108 and described above in Eqn. (4); a global SAR constraint, as indicated at 110 and described above in Eqn. (5); a peak power constraint, as indicated at 112 and described above in Eqn. (6); and an average power constrain, as indicated at 114 and described above in Eqn. (7). In addition, the local SAR constraint 108 and the global SAR constraint 110 may be assessed using compressed SAR matrices, which may be VOPs, thereby reducing the computational complexity of the RF design process. Furthermore, the optimization process at step 106 may also take into consideration other factors including RF frequency, number of RF channels, and others. Then, the method proceeds by providing the determined optimal RF waveforms to a MRI system, as indicated at step 116. The MRI system is then capable of employing these RF waveforms to produce pTx RF pulses to achieve a target RF treatment objective, such as a target temperature, or local energy deposition.

Figure 2:
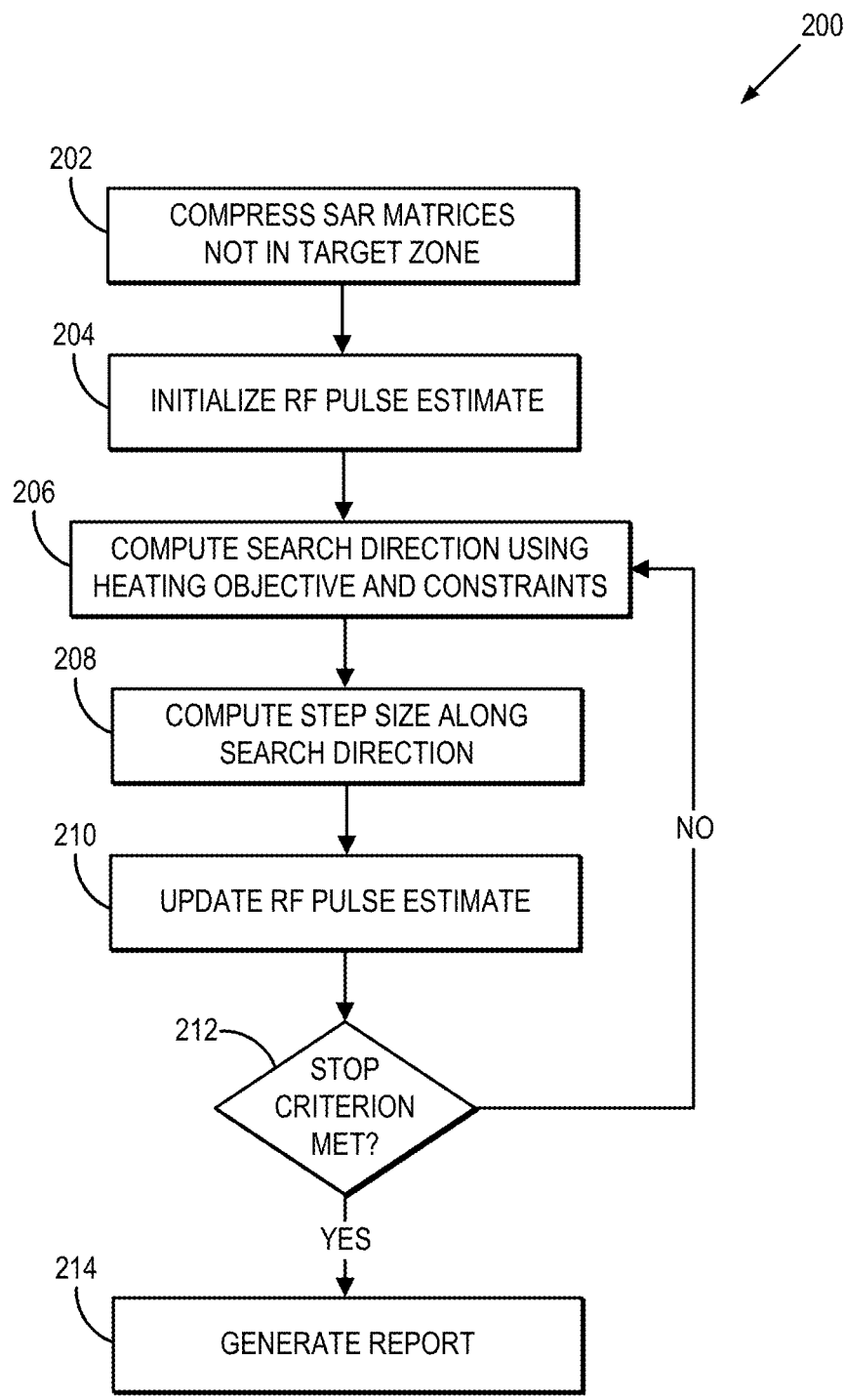
FIG. 2 is a flowchart setting forth the step of an example optimization process.

Referring now to FIG. 2, a flowchart setting forth steps of an example primal-dual constrained optimization process 200, for use in accordance with the present invention is shown, although other constrained algorithms may be used as well. The process 200 begins at process block 202 where provided or computed SAR matrices may be compressed, for example, using a virtual observation point approach. In some aspects, it may be desirable to compress SAR matrices not included in target regions.

Then, at process block 204 an initial estimate for the RF pulse, $b=b_0$, may be generated, for example, with pulses amplitudes set to zero voltage. At process block 206, a search direction, D, at b may be computed from knowledge of the heating objective function and SAR and power constraint derivates, in accordance with Eqns. (3)-(7). This can be achieved by using a Newton step (local quadratic approximation of the objective function), although other techniques to compute the search direction may also be used. Then at process block 208 a step size $\alpha$ along the search direction is computed in accordance with the biggest increase in energy deposition, or target heating, possible, and RF pulse that does not violate the power constraints and does not create SAR values greater than what is deemed safe in non-target regions. For example, the line search may be performed using a backtracking techniques, although other methods are possible.

At process block 210, an updated estimate of the RF pulse is obtained using $b=b+\alpha \cdot D$ from previous calculations. Steps 206-210 may then be repeated as necessary until a convergence criterion to stop the loop is met, as determined at decision block 212. For example, a criterion for convergence can be when the norm of the Newton residual is smaller than a predefined value. Then, at process block 214 a report is generated, which may take any shape or form. Such report may send instructions to an RF pulse sequence server for generating RF pulses, as optimized, which may then be submitted to and used by an MRI system. In some aspects, computations according to process 200 may also be used to generate SAR or temperature maps, which may be included in the report generated at process block 214, as shown in FIGS. 7-10.

Figure 3:
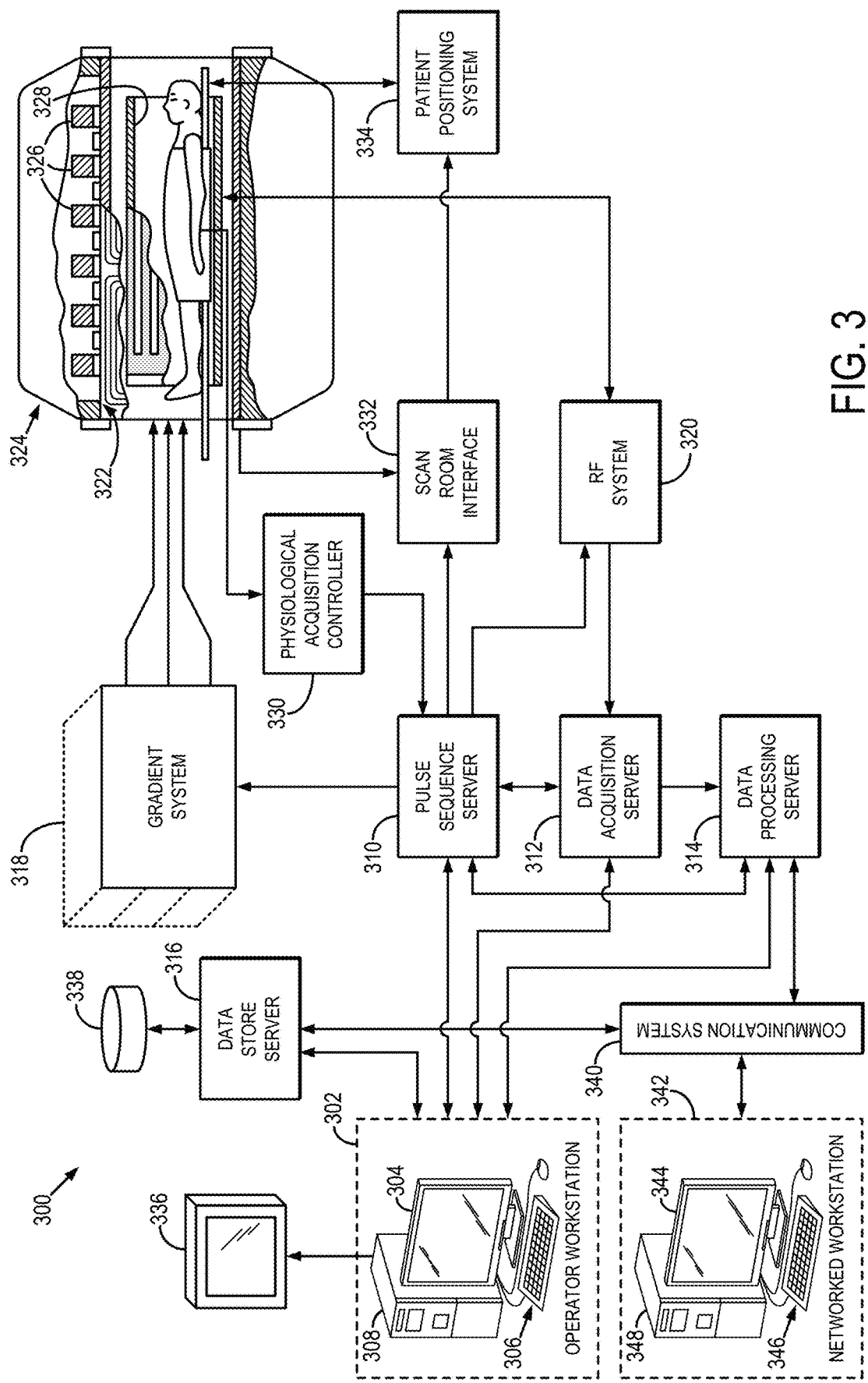
FIG. 3 is a block diagram of an example of an MRI system that can implement the present invention.

Referring particularly now to FIG. 3, an example of a magnetic resonance imaging ("MRI") system 300 that can implement the present invention is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328. The whole-body RF coil 328 may include a single-channel transmit coil or a multiple-channel transmit coil array that is capable of implementing the method of the present invention. For instance, the whole-body RF coil 328 may include a two channel transmit coil array.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes one or more RF transmitters for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (8)$$

and the phase of the received magnetic resonance signal may also be determined according to the following relationship:

$$\varphi = \tan^{-1}\left(\frac{Q}{I}\right). \quad (9)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 304 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

Figure 4:
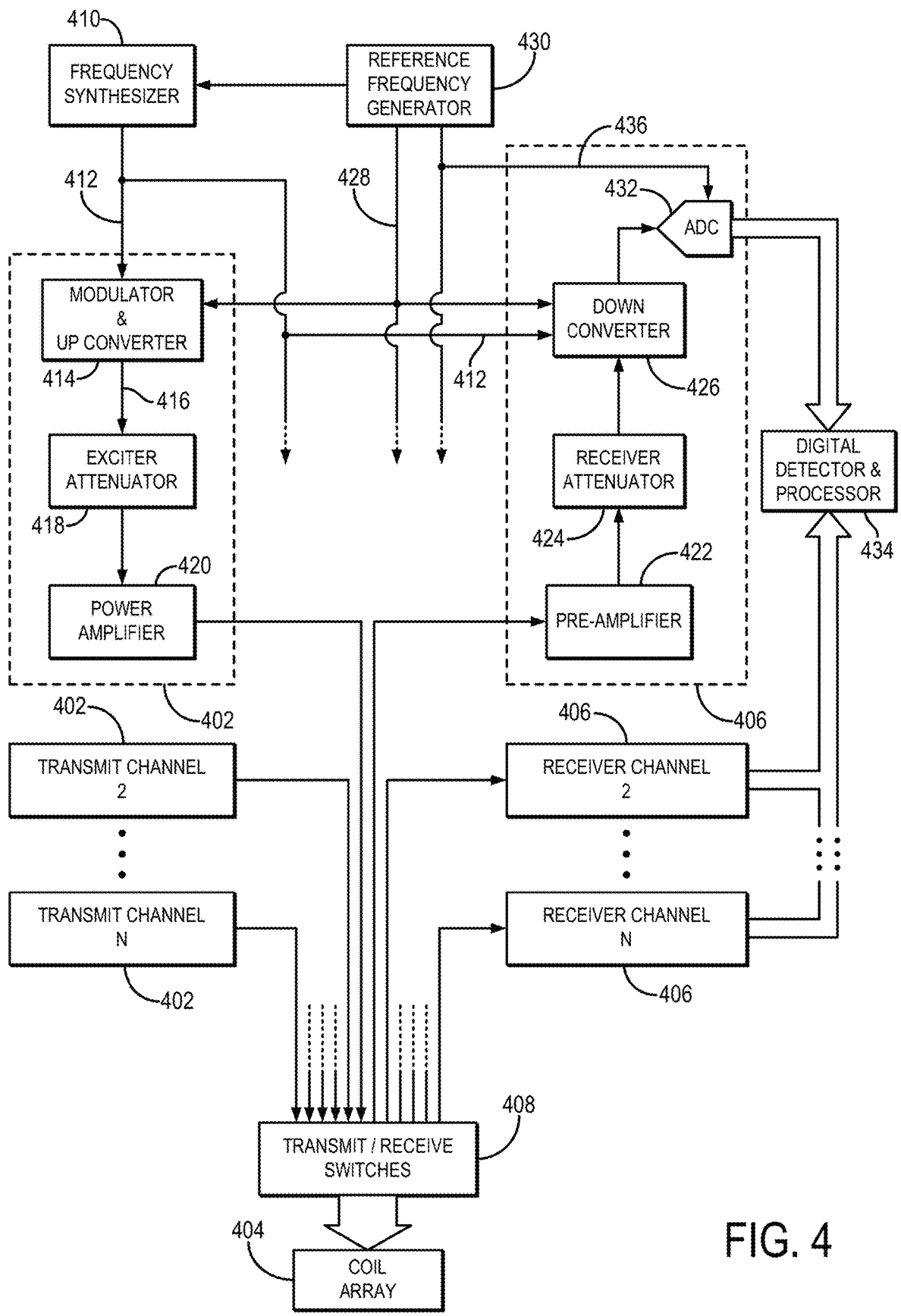
FIG. 4 is a block diagram of an example of a parallel transmit and receive RF system that can form a part of the MRI system of FIG. 3.

As shown in FIG. 3, the RF system 320 may be connected to the whole-body RF coil 328, or, as shown in FIG. 4, a transmission section of the RF system 320 may connect to one or more transmit channels 402 of an RF coil array 404 and a receiver section of the RF system may connect to one or more receiver channels 406 of the RF coil array 404. The transmit channels 402 and the receiver channels 406 are connected to the RF coil array 404 by way of one or more transmit/receive ("T/R") switches 408. In alternative configurations of the RF system 328 in which the receive coils are a separate collection of coils than the transmit coils, T/R switches 408 are not needed and are not used. Instead, in such a configuration the receive array is "detuned" during transmission so that it does not couple to the transmitter. Likewise, during reception, the transmitter is detuned. In this manner, the transmit and receive paths do not mix.

Referring particularly to FIG. 4, the RF system 320 includes one or more transmit channels 402 that produce a prescribed RF excitation field. The base, or carrier, frequency of this RF excitation field is produced under control of a frequency synthesizer 410 that receives a set of digital signals from the pulse sequence server 310. These digital signals indicate the frequency and phase of the RF carrier signal produced at an output 412. The RF carrier is applied to a modulator and up converter 414 where its amplitude is modulated in response to a signal, R(t), also received from the pulse sequence server 310. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 416 may be attenuated by an exciter attenuator circuit 418 that receives a digital command from the pulse sequence server 310. The attenuated RF excitation pulses are then applied to a power amplifier 420 that drives the RF coil array 404.

The MR signal produced by the subject is picked up by the RF coil array 402 and applied to the inputs of the set of receiver channels 406. A preamplifier 422 in each receiver channel 406 amplifies the signal, which is then attenuated by a receiver attenuator 424 by an amount determined by a digital attenuation signal received from the pulse sequence server 310. The received signal is at or around the Larmor frequency, and this high frequency signal is down converted in a two step process by a down converter 426. The down converter 426 first mixes the MR signal with the carrier signal on line 412 and then mixes the resulting difference signal with a reference signal on line 428 that is produced by a reference frequency generator 430. The down converted MR signal is applied to the input of an analog-to-digital ("A/D") converter 432 that samples and digitizes the analog signal. As an alternative to down conversion of the high frequency signal, the received analog signal can also be detected directly with an appropriately fast analog-to-digital ("A/D") converter and/or with appropriate undersampling. The sampled and digitized signal is then applied to a digital detector and signal processor 434 that produces 16-bit in-phase (I) values and 16-bit quadrature (Q) values corresponding to the received signal. The resulting stream of digitized I and Q values of the received signal are output to the data acquisition server 312. In addition to generating the reference signal on line 428, the reference frequency generator 430 also generates a sampling signal on line 436 that is applied to the A/D converter 432.

In summary, the present invention provides systems and methods directed to design and delivery of RF pulses using RF phased arrays for use in focused RF-based treatment. Among other uses, the present invention may be implemented to achieve temperature elevations (hyperthermia treatment) or to activate thermoresponsive polymers for targeted drug release via optimized RF pulses, designed in accordance with subject energy absorption or temperature limitations, as well as hardware constraints. Such RF-based treatment may be monitored or controlled using any methods or systems configured to do so. For example, imaging may be performed continuously, intermittently, or interleaved with RF-based treatment, in order to verify or control temperature profiles or hotspots, in target or non-target regions. In addition, imaging information may also be utilized in designing or updating RF waveforms.

In some aspects of the present invention, RF-based treatment may be achieved via appropriately configured MRI systems. In particular, the present invention recognizes that RF phased arrays, commonly used for imaging in combination with MRI scanners, may be used in hyperthermal RF-based treatment procedures. Contrary to previous efforts that aim to reduce or minimize energy deposition in subjects imaged using MRI systems, the present invention provides for creating localized or wide area temperature elevations in target treatment areas using RF phased arrays via optimized RF pulses. This approach facilitates combining MR imaging with RF-based treatments to provide information for accurate localization, monitoring or control of RF-based treatment. For example, many types of available MRI sequences can be used to monitor treatment, such as temperature maps, T1-weighted images, and so forth, and the present invention is not limited to a single one of them. In addition, the frequency of the RF-based treatment process may not necessarily be required to match the imaging frequency of an MR scanner employed. However, in the case that it does, then the same RF phased array can be used both for both RF treatment and monitoring.

Therefore, the approach of present invention may be advantageously integrated within or combined with MRI systems. Such implementations might not present the magnetic compatibility problems encountered when combining external RF treatment devices or systems with MRI scanners. Hence, a complete integration of treatment (heating) and monitoring (imaging) protocols can be achieved. By contrast, most ultrasound and ionizing devices are generally incompatible with the magnetic fields generated by an MRI system, and development of MRI-safe devices that are compatible with those fields is a significant engineering challenge that may not be met for all devices.

In some envisioned configurations, RF-based treatment may be achieved by way of independent, or external RF phased array devices or systems configured with capabilities for design and delivery of optimized RF pulses. In such cases, monitoring or control of RF-based treatment may also be achieved using any systems appropriate for doing so, which may include systems other than MRI.

Features suitable for combinations and sub-combinations would be readily apparent to persons skilled in the art upon review of the present application as a whole. The subject matter described herein and in the recited claims intends to cover and embrace all suitable changes in technology.

The invention claimed is:

1. A method for designing parallel transmission (pTx) radiofrequency (RF) pulses for use in an RF treatment, the method comprising:
   a) selecting a target region in a subject;
   b) providing a plurality of specific absorption rate (SAR) matrices for estimation of SAR at locations within the subject;
   c) determining a first set of SAR matrices for locations in the target region using the provided SAR matrices;
   d) determining a second set of SAR matrices for locations in the subject not in the target region using the provided SAR matrices; and
   e) using a processor, designing a plurality of RF pulses for achieving a target power deposition in the target region by using the first set of SAR matrices and the second set of SAR matrices in an optimization that determines a set of RF waveforms that produce a target average local SAR using the first set of SAR matrices while minimizing a local SAR and a global SAR using the second set of SAR matrices; and
   f) using the processor, controlling a plurality of RF coils and a parallel transmitter using the set of RF waveforms to provide an excitation to the subject.

2. The method of claim 1, wherein the method further comprises providing a model of the subject's anatomy.

3. The method of claim 2, wherein providing the plurality of SAR matrices in step b) includes producing the plurality of SAR matrices, which includes computing, using the model of the subject's anatomy, a propagation of electromagnetic fields created by an RF array.

4. The method of claim 1, wherein the method further comprises providing a plurality of compressed SAR matrices that define estimates for either or both of the first and second set SAR matrices for locations within and outside the target region.

5. The method of claim 1, wherein the set of RF waveforms determined in step e) also minimizes a peak power in each of a plurality of transmit channels.

6. The method of claim 1, wherein the set of RF waveforms determined in step e) also minimizes an average power in each of a plurality of transmit channels.

7. The method of claim 1, wherein the method further comprises providing a sequential excitation to the subject using the plurality of RF pulses, wherein the RF pulses are delivered in time segments in dependence of a plurality of transmit channels.

8. The method of claim 1, wherein the set of RF waveforms determined in step e) provide an enhanced sensitivity to at least one of a biological agent and a chemical agent by achieving a target temperature in the target zone.

9. The method of claim 1, wherein the method further comprises providing the set of RF waveforms to a magnetic resonance imaging system.

10. An apparatus for hyperthermia treatment comprising:
    a plurality of radio frequency (RF) coils configured to generate an RF field in a subject to receive a hyperthermia treatment;
    a parallel transmitter configured to receive RF waveforms and to direct the plurality of RF coils to generate the RF field based on the received RF waveforms; and
    a computer system in communication with the parallel transmitter and programmed to:
    a) select a target region in a subject;
    b) provide a plurality of specific absorption rate (SAR) matrices that define estimates of SAR at locations within the subject;
    c) determine a first set of SAR matrices for locations in the target region using the provided SAR matrices;
    d) determine a second set of SAR matrices for locations not in the target region using the provided SAR matrices;
    e) design a plurality of RF pulses for achieving a target power deposition in the target region based on an optimization that uses the first set of SAR matrices and the second set of SAR matrices;
    f) control the plurality of RF coils and the parallel transmitter using a set of RF waveforms formed from the plurality of RF pulses that direct the parallel transmitter to generate an RF field that achieves a target average local SAR in the target region while minimizing a local SAR and a global SAR outside the target region.

11. The apparatus of claim 10, wherein the computer system is further programmed to provide a model of the subject's anatomy.

12. The apparatus of claim 11, wherein the computer is further programmed to provide the plurality of SAR matrices by producing the plurality of SAR matrices, wherein the computer system is programmed to compute, using the model of the subject's anatomy, a propagation of electromagnetic fields created by the plurality of RF coils.

13. The apparatus of claim 10, wherein the computer system is further programmed to provide a plurality of compressed SAR matrices that define estimates for either or both of the first and second set SAR matrices for locations within and outside the target region.

14. The apparatus of claim 10, wherein the computer system is further programmed to determine the set of RF waveforms such that the set of RF waveforms minimizes a peak power in each of a plurality of transmit channels in the parallel transmitter.

15. The apparatus of claim 10, wherein the computer system is further programmed to determine the set of RF waveforms such that the set of RF waveforms minimizes an average power in each of a plurality of transmit channels in the parallel transmitter.

16. The apparatus of claim 10, wherein an RF system including the plurality of coils is configured to provide a sequential excitation to the subject using the plurality of RF pulses, wherein the RF pulses are delivered in time segments in dependence of a plurality of transmit channels in the parallel transmitter.

17. The apparatus of claim 10 wherein the set of RF waveforms provide an enhanced sensitivity to a biological agent by achieving a target temperature in the target zone.

18. The apparatus of claim 10, further comprising:
- a magnet system configured to generate a polarizing magnetic field about at least a portion of a subject;
- a plurality of gradient coils configured to apply at least one magnetic field gradient to the polarizing magnetic field; and
- a radio frequency (RF) system configured to receive magnetic resonance signals from the subject.

19. The apparatus of claim 18, wherein the computer system is further programmed to create a map indicative of an RF treatment of the subject using magnetic resonance signals received using the RF system.

20. The apparatus of claim 19, wherein the computer system is further programmed to adjust the target power deposition using the map that is indicative of the RF treatment of the subject.

\* \* \* \* \*